United States Patent [19]

Bakshi

[11] 4,123,442
[45] Oct. 31, 1978

[54] REGENERATION OF MALEIC ANHYDRIDE VANADIUM-PHOSPHORUS-OXYGEN CATALYST BY CONTACTING WITH SULFUR TRIOXIDE

[75] Inventor: Kiran R. Bakshi, El Cerrito, Calif.

[73] Assignee: Chevron Research Company, San Francisco, Calif.

[21] Appl. No.: 809,735

[22] Filed: Jun. 24, 1977

[51] Int. Cl.$^2$ .................. C07D 307/60; B01J 27/28; B01J 23/92
[52] U.S. Cl. ..................... 260/346.75; 252/411 R; 252/416
[58] Field of Search ............... 252/411, 416, 413, 415, 252/435, 437; 260/346.75

[56] References Cited

U.S. PATENT DOCUMENTS

| | | | |
|---|---|---|---|
| 3,919,259 | 11/1975 | Shier | 260/346.75 |
| 3,985,775 | 10/1976 | Harrison | 252/437 |
| 4,020,174 | 4/1977 | Partenheimer | 252/415 |

FOREIGN PATENT DOCUMENTS 7,314,746  5/1974  Netherlands .................. 252/411 R Primary Examiner—P. E. Konopka
Attorney, Agent, or Firm—D. A. Newell; John Stoner, Jr.; A. T. Bertolli

[57] ABSTRACT

The catalytic properties of a complex catalyst comprising vanadium, phosphorus and oxygen which is used for the oxidation of hydrocarbons to maleic anhydride can be partially regenerated by contacting the catalyst with sulfur trioxide.

13 Claims, 1 Drawing Figure

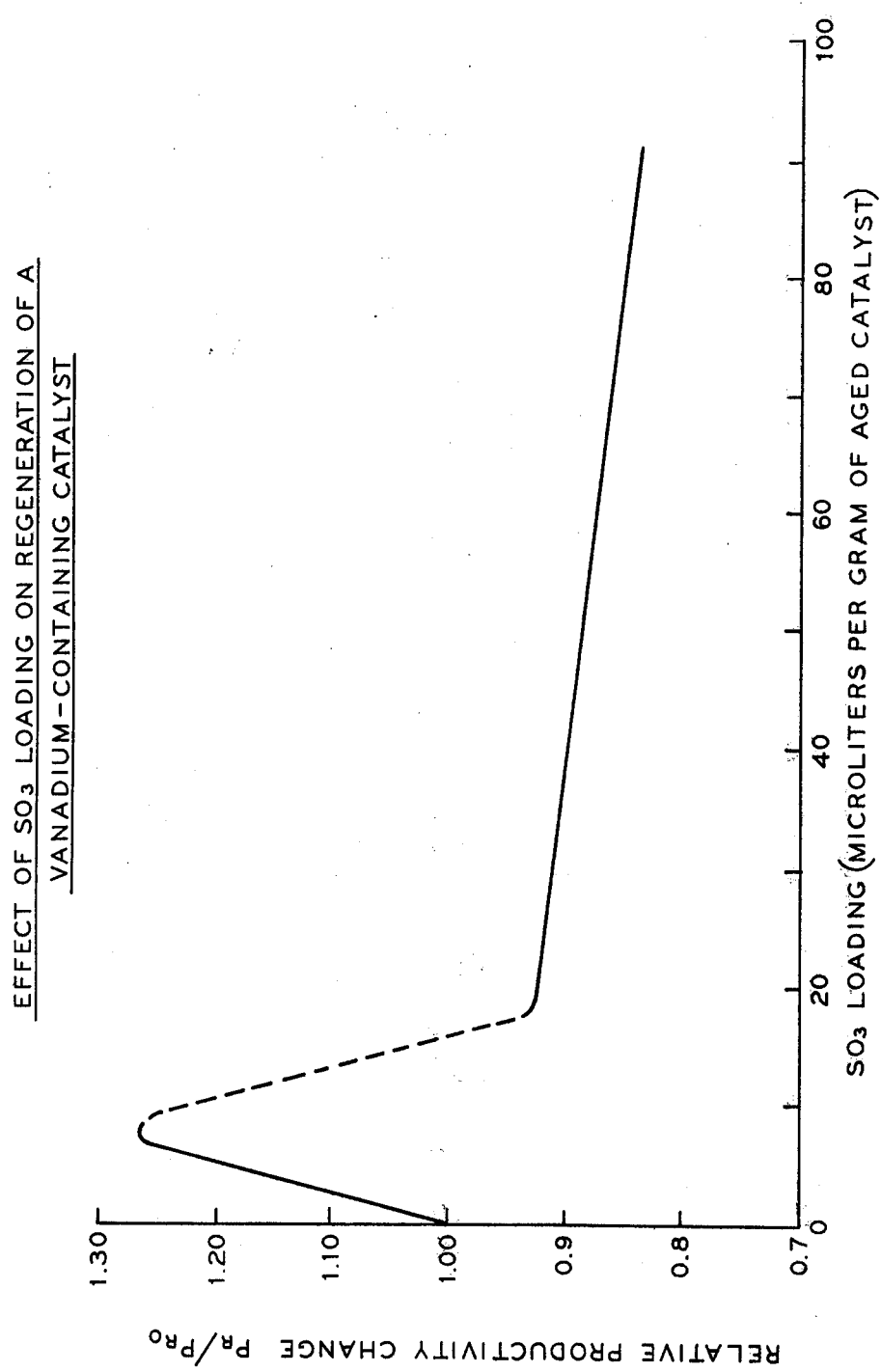

REGENERATION OF MALEIC ANHYDRIDE VANADIUM-PHOSPHORUS-OXYGEN CATALYST BY CONTACTING WITH SULFUR TRIOXIDE

BACKGROUND OF THE INVENTION

The invention concerns a method for partially regenerating the catalytic properties of an aged maleic anhydride catalyst. In particular, it has been found that the catalytic properties of a vanadium-phosphorus-oxygen oxidation catalyst used in the conversion of hydrocarbons to maleic anhydride can be partially regenerated by contacting the aged catalyst with sulfur trioxide.

Maleic anhydride is a commercially valuable chemical. It can be used alone or with other acids in the manufacture of alkyd and polyester resins. It is a versatile chemical intermediate also useful as a monomer to produce various copolymers, such as the copolymer of maleic anhydride and vinyl acetate. Significant quantities of maleic anhydride are produced each year to satisfy these needs.

The prior art teaches that maleic anhydride can be produced by oxidizing hydrocarbons, such as butane, butene, butadiene and benzene. The oxidation is carried out in the presence of an oxidation catalyst. The prior art further teaches that vanadium-phosphorus-oxygen catalysts are especially active to catalyze the vapor-phase oxidation of hydrocarbons to maleic anhydride. For instance, the high-surface-area catalyst described in U.S. Pat. No. 3,864,280, granted to Schneider on Feb. 4, 1975, provides high yields of maleic anhydride from butane. These catalysts comprise a vanadium-phosphorus-oxygen complex having an intrinsic surface area in the range from about 7 to 50 square meters per gram, a phosphorus to vanadium atomic ratio in the range of 0.9–1.8:1, and an average vanadium valence in the range 3.9 to 4.6.

During the oxidation process, the catalyst is contacted with hydrocarbon under reducing conditions. Typically the oxidation is carried out at from about 300° C. to about 500° C. In practice, an oxidation feed gas is fed to a tube reactor containing the catalyst material. Shortly into the reactor the hydrocarbon begins to oxidize rapidly thus creating a hot-spot. It has been observed that as the time of reaction on the catalyst increases, the activity and selectivity of the catalyst decreases. This is called "catalyst aging."

Accordingly, it is desirable to find a process for regenerating catalytic properties of aged catalyst to regain the initial high catalyst activity and selectivity. The selection of a suitable regenerating agent and the regeneration conditions which are used are critical, since over-regeneration of the catalyst has been found to result in a very non-selective catalyst. U.S. Pat. No. 4,020,174, issued to Partenheimer on Apr. 26, 1977, describes the use of regenerating agents to reactivate the catalytic properties of vanadium-phosphorus-oxygen catalysts. The agents are selected from the halide-containing compounds.

SUMMARY OF THE INVENTION

This invention provides a method for regenerating a vanadium-containing oxidation catalyst used in the production of maleic anhydride by contacting aged catalyst with a sufficient amount of sulfur trioxide to regenerate the vanadium-containing catalyst by raising the average vanadium valence to a value below 5.0, preferably from about 3.9 to about 4.6.

BRIEF DESCRIPTION OF THE FIGURE

The following detailed description refers to the accompanying FIGURE, which graphically illustrates one example of the relationship between the relative productivity change for a preferred high surface area catalyst and the amount of sulfur trioxide used to regenerate the catalytic properties.

DETAILED DESCRIPTION OF THE INVENTION

This invention provides a process for partially regenerating a vanadium-containing catalyst used in the oxidation of hydrocarbons to maleic anhydride by contacting aged catalyst with sulfur trioxide. Catalyst regeneration using sulfur trioxide is visualized as an equilibrium between a reduced catalyst site in contact with sulfur trioxide and an oxidized catalyst site in the presence of sulfur dioxide. The forward step of the equilibrium, that is the reaction of sulfur trioxide ($SO_3$) with a reduced catalyst site is extremely fast and can occur even at very low $SO_3$ concentrations. It has been found that catalyst selectivity for maleic anhydride improves almost linearly with the amount of $SO_3$ contacted with the aged catalyst. However, it has been unexpectedly found that this improvement does not continue with increasing amounts of $SO_3$. In other words, for any given catalyst there is an optimum $SO_3$ level. If the amount of $SO_3$ contacted per gram of catalyst is above the optimum level then the selectivity of the catalyst begins to decrease until for many catalysts it may drop below the aged level.

The regeneration process can be carried out in situ or by external methods. In-situ regeneration offers the advantage of a continuous operation which can be carried out in the reactor vessel under normal operating conditions, but also necessitates the use of corrosion-resistant equipment.

The in-situ regeneration can be carried out by injecting a known amount of liquid $SO_3$ into the feed stream to the reactor. The reactor can be maintained at normal operating conditions during the $SO_3$ injection. Accordingly, suitable conditions for in-situ regeneration include a temperature from about 20° C., preferably about 200° C. to about 600° C., most preferably from about 300° C. to about 450° C.; and a pressure from about atmospheric up to about 100 psig, preferably from about 4 to about 50 psig, and most preferably about 4 to 10 psig.

External regeneration can be carried out by removing the aged catalyst from the reactor and charging it to a stainless-steel vessel, drying the catalyst, and then injecting $SO_3$ into the vessel while heating to temperatures in the range as specified for the in-situ regeneration.

Using either an in-situ or an external regeneration method, catalyst productivity can be increased as much as about 25%. Accordingly, a significant improvement in catalyst life can be obtained by periodically treating the catalyst with $SO_3$, or by continuously feeding low concentrations of $SO_3$ in the feed stream.

It has been found that initially catalyst selectivity improves almost linearly with the amount of $SO_3$ contacted with aged catalyst. However, it has been unexpectedly found this improvement does not continue with increasing amounts of $SO_3$. For any given vanadium-containing catalyst, there is an optimum amount of $SO_3$ which can be used in the regeneration process. If the amount of SO₃ contacted with aged catalyst exceeds the optimum level, the selectivity of the catalyst begins to decrease until for many catalysts it may actually drop below the selectivity of the untreated aged catalyst. The relationship between selectivity and the amount of SO₃ used in the regeneration process often varies for differing catalysts, such that the optimum amount of SO₃ will not be the same for all vanadium-containing catalysts. However, as a general rule, the optimum amount of SO₃ per gram of aged catalyst can be determined by considering the effect of SO₃ on the average vanadium valence of the catalyst. It has been found that about 13.5 microliters of SO₃ will raise the average vanadium valence of one gram of aged catalyst by a valence value of 0.1. Since vanadium-containing catalysts are known to have a preferred average vanadium valence, the optimum amount of SO₃ per gram of aged catalyst can be closely approximated by substracting the average vanadium valence of the aged catalyst ($\bar{V}_{aged}$) from the preferred average vanadium valence of that catalyst ($\bar{V}_{desired}$) and multiplying the remainder of 135 microliters. This calculation can be represented by the equation:

$$(SO_3) \text{ optimum per gram of aged catalyst} = 135 (\bar{V}_{desired} - \bar{V}_{aged}) \mu l$$

Accordingly, in a preferred embodiment of this invention aged vanadium-containing catalyst is regenerated by contacting each gram of aged catalyst with an amount of SO₃ determined by multiplying the desired change in average vanadium valence of the aged catalyst by 135 microliters. In any event, care should be exercised when using amounts of SO₃ above the optimum, since for many catalysts such amounts may either give very little benefit or actually further degenerate the already aged catalyst.

The following example illustrates practice of this invention. Other embodiments consistent with the invention will be apparent from the example. Accordingly, the example is not intended to limit the scope of the claims which follow.

EXAMPLE

Using a catalyst prepared according to U.S. Pat. No. 3,864,280, herein incorporated by reference, butane was oxidized to maleic anhydride.

This oxidation was carried out continuously for one year to obtain an aged catalyst. Aliquots of the aged catalyst were tested for selectivity and then regenerated by both in-situ and external treatment methods. In-situ regeneration was carried out by injecting SO₃ (Allied Chemicals, Sulfan) into the test reactor feed stream while maintaining the vessel at the normal operating conditions as listed in Table I. About 1 hour after in-situ treatment, a test run was started to evaluate catalyst performance. External regeneration was carried out by placing the aged catalyst in a ½-inch stainless-steel tube and drying the catalyst at 300° C. in flowing inert gas for approximately 8 hours. After drying, SO₃ was injected into the tube and the catalyst was heated to 300° C. for 2 to 3 hours. Following the SO₃ treatment, the catalyst was replaced in the test reactor vessel and reevaluated for performance. The test conditions are summarized in Table I and the results of the tests are summarized in Table II.

TABLE I

| RUN CONDITIONS | |
|---|---|
| Temperature | 705° F (375° C) |
| Pressure | 4.5 psig |
| Feed butane concentration | 2.55 % by vol. |
| Feed oxygen concentration | 10% by vol. |
| Amount of catalyst | 11 grams |
| Butane feed rate | 12 cc/hour |
| Total gas flow rate | 1.72 liters/minute |

TABLE II

| | EFFECTS OF REGENERATION | | |
|---|---|---|---|
| Run No. | SO₃ Level microliters/ gram Catalyst | Method | Catalyst Productivity $P_R$* lb/hr-ft³ | Relative Change $P_R/P_{R_O}$ |
| 1 | — | — | 1.67 | 1.00 ($P_{R_O}$) |
| 2 | 1.40 | In-situ | 1.69 | 1.02 |
| 3 | 3.33 | In-situ | 1.87 | 1.12 |
| 4 | 4.54 | External | 1.91 | 1.14 |
| 5 | 6.56 | External | 2.10 | 1.26 |
| 6 | 18.18 | External | 1.51 | 0.90 |
| 7 | 18.18 | External | 1.57 | 0.94 |
| 8 | 90.9 | External | 1.41 | 0.84 |

*Under standard run conditions given in Table I

In Table II, productivity is defined as the pounds of maleic anhydride produced per hour per cubic foot of reactor volume.

The Figure accompanying this description was obtained by plotting the SO₃ level against the relative change in productivity. As can be seen, with up to the optimum of about about 8 microliters of SO₃ per gram of catalyst the productivity increased almost linearly with SO₃ level. At SO₃ levels between about 8 microliters/g and about 15 microliters/g, productivity was improved, but unexpectedly decreased with increasing SO₃ level. At SO₃ levels above about 15 microliters/g, catalyst productivity was actually degraded below the productivity of the untreated aged catalyst.

In this case, the 26% improvement for example Run No. 5 returns the catalyst to a performance level it had at about half of its total life, before regeneration. Thus, catalyst life can be significantly extended with SO₃ regeneration.

What is claimed is:

1. A process for partially regenerating the catalytic properties of an aged vanadium-phosphorus-oxygen catalyst used in the oxidation of hydrocarbons to maleic anhydride, which comprises contacting the aged catalyst with sulfur trioxide under conditions effective to increase the average vanadium valence of the aged catalyst to a value from about 3.9 to about 4.6.

2. A process according to claim 1 wherein the hydrocarbon is butane.

3. A process according to claim 1 wherein regeneration is carried out during the course of said oxidation of hydrocarbons.

4. A process according to claim 1 wherein regeneration is carried out at a temperature of from about 20° C. to about 600° C.

5. A process according to claim 1 wherein the aged catalyst is contacted with an amount of sulfur trioxide in microliters per gram of aged catalyst up to an amount equal to about 135 times the difference between the initial average vanadium valence of the catalyst and the average vanadium valence of the aged catalyst.

6. A process according to claim 1 wherein the regenerated catalyst comprises vanadium, phosphorus and oxygen and has an intrinsic surface area in the range of from about 7 to 50 square meters per gram, a phosphorus to vanadium atomic ratio in the range 0.9–1.8 to 1, and an average vanadium valence in the range 3.9 to 4.6.

7. A process according to claim 6 wherein said catalyst is contacted with from about 3 to 13 microliters of $SO_3$ per gram of catalyst.

8. A process according to claim 7 wherein said catalyst is contacted with about 8 microliters of $SO_3$ per gram of catalyst.

9. In a process for production of maleic anhydride from the oxidation of hydrocarbons which comprises contacting said hydrocarbon in the vapor phase with a solid complex catalyst comprising a vanadium-phosphorus-oxygen complex having an intrinsic surface area in the range from about 7 to 50 square meters per gram, a phosphorus to vanadium atomic ratio in the range 0.9–1.8:1, and an average vanadium valence in the range 3.9 to 4.6, wherein the catalytic properties of the catalyst for the production of maleic anhydride from said hydrocarbon have decreased from a level achieved during earlier catalyst life; the improvement which comprises contacting said aged catalyst complex with sulfur trioxide under conditions effective to increase the average vanadium valence of the aged catalyst to a value from about 3.9 to about 4.6.

10. A process according to claim 9 wherein the aged catalyst is contacted with an amount of sulfur trioxide in microliters per gram of aged catalyst up to an amount equal of about 135 times the difference between the initial average vanadium valence of the catalyst and the average vanadium valence of the aged catalyst.

11. A process according to claim 10 wherein said hydrocarbon comprises normal butane.

12. A process according to claim 9 wherein said catalyst is contacted with from about 3 to 13 microliters of $SO_3$ per gram of catalyst.

13. A process according to claim 9 wherein said catalyst is contacted with about 8 microliters of $SO_3$ per gram of catalyst.

* * * * *

UNITED STATES PATENT AND TRADEMARK OFFICE
CERTIFICATE OF CORRECTION

PATENT NO. : 4,123,442

DATED : October 31, 1978

INVENTOR(S) : Kiran R. Bakshi

It is certified that error appears in the above-identified patent and that said Letters Patent are hereby corrected as shown below:

Column 3, line 22, "of" should read --by--.

Signed and Sealed this

Third Day of April 1979

[SEAL]

Attest:

RUTH C. MASON
Attesting Officer

DONALD W. BANNER
Commissioner of Patents and Trademarks